ized cochlear area, or, while receiving some music notes, each electrode is enabled to pick up a characteristic frequency signal of a music note generated in a corresponding musical response area so as to improve the accuracy of musical melody perception and to enhance the music listening experience.

US 11,123,550 B2

(12) United States Patent
Tian et al.

(10) Patent No.: US 11,123,550 B2
(45) Date of Patent: Sep. 21, 2021

(54) COCHLEA ELECTRODE ARRANGEMENT, DEVICE, SYSTEM AND METHOD FOR ENHANCING MUSICAL MELODY PERCEPTION

(71) Applicant: SHANDONG UNIVERSITY, Shandong (CN)

(72) Inventors: Lan Tian, Jinan (CN); Yong Wang, Jinan (CN); Xiaoshan Lu, Jinan (CN); Xu Tian, Jinan (CN)

(73) Assignee: SHANDONG UNIVERSITY, Jinan (CN)

(*) Notice: Subject to any disclaimer, the term of this patent is extended or adjusted under 35 U.S.C. 154(b) by 81 days.

(21) Appl. No.: 15/575,078

(22) PCT Filed: Dec. 1, 2016

(86) PCT No.: PCT/CN2016/108235
§ 371 (c)(1),
(2) Date: Nov. 17, 2017

(87) PCT Pub. No.: WO2017/128856
PCT Pub. Date: Aug. 3, 2017

(65) Prior Publication Data
US 2018/0353752 A1 Dec. 13, 2018

(30) Foreign Application Priority Data

Jan. 27, 2016 (CN) .......................... 201610056261.4
Jan. 27, 2016 (CN) .......................... 201610060626.0

(51) Int. Cl.
*A61N 1/05* (2006.01)
*A61N 1/36* (2006.01)
(Continued)

(52) U.S. Cl.
CPC ............. *A61N 1/0541* (2013.01); *A61N 1/05* (2013.01); *A61N 1/36036* (2017.08);
(Continued)

(58) Field of Classification Search
USPC .......................................................... 607/54
See application file for complete search history.

(56) References Cited

U.S. PATENT DOCUMENTS 4,819,647 A * 4/1989 Byers .................. A61N 1/0541
128/903
2005/0107843 A1* 5/2005 McDermott ....... A61N 1/36036
607/57
(Continued)

FOREIGN PATENT DOCUMENTS

CN     102625220 A    8/2012
CN     103325381 A    9/2013
(Continued)

OTHER PUBLICATIONS

Feb. 9, 2017 International Search Report issued in International Patent Application No. PCT/CN2016/108235.
(Continued)

*Primary Examiner* — Nicole F Johnson
(74) *Attorney, Agent, or Firm* — Oliff PLC (57) ABSTRACT

A cochlea electrode arrangement, system and method for enhancing musical melody perception. On each cochlear basilar membrane, according to the characteristic frequency correspondence of music notes, a phonosensitive full spectrum band corresponding to the cochlea apex to cochlea base is divided into musical response areas in response to specific musical note stimulating signals; a corresponding electrode for conducting or sensing frequency band signals is placed in each musical response area, namely, each electrode is placed in the corresponding characteristic frequency band
(Continued)

where the music notes are located, the electrodes are divided into two groups, and a corresponding group of electrodes is implanted into cochleae on two sides respectively. Due to the fact that the electrodes are arranged in the cochleae on the two sides, the cochlea electrode arrangement is easy to implement, and the electrodes arranged in the cochleae on the two sides can perceive music better.

8 Claims, 3 Drawing Sheets

(51) Int. Cl.
 *A61N 1/372* (2006.01)
 *H04R 25/00* (2006.01)
(52) U.S. Cl.
 CPC ..... *A61N 1/36038* (2017.08); *A61N 1/37217* (2013.01); *H04R 25/505* (2013.01); *G10H 2210/066* (2013.01); *G10H 2240/026* (2013.01); *H04R 25/554* (2013.01); *H04R 2225/67* (2013.01)

(56) References Cited

U.S. PATENT DOCUMENTS

| | | | | |
|---|---|---|---|---|
| 2006/0029912 | A1* | 2/2006 | Kearby | G09B 5/04 434/116 |
| 2010/0249879 | A1* | 9/2010 | Bracker | A61N 1/36039 607/56 |
| 2010/0274560 | A1 | 10/2010 | Goorevich et al. | |
| 2012/0226332 | A1* | 9/2012 | Chambers | A61N 1/3782 607/57 |
| 2014/0277276 | A1* | 9/2014 | Saoji | A61N 1/36039 607/57 |

FOREIGN PATENT DOCUMENTS

| | | |
|---|---|---|
| CN | 104013480 A | 9/2014 |
| CN | 105596119 A | 5/2016 |
| CN | 105596120 A | 5/2016 |
| CN | 205515041 U | 8/2016 |

OTHER PUBLICATIONS

Charles J. Lim et al., "Technological, Biological, and Acoustical Constraints To Music Perception in Cochlear Implant Users", Hearing Research, vol. 308, pp. 13-26, 2014.
Lichuan Ping et al., "Musical Pitch Discrimination By Cochlear Implant Users", Annals Publishing Company, Annals of Otology, Rhinology & Laryngology, 121(5):328-336, pp. 328-336, 2012.
Guy Rebillard et al., "The Transfer of Airborne Sound Vibration to the Structures and Fluid of the Cochlea", Cochlea: Function, retrieved from http://www.cochlea.eu/en/cochlea/function, last updated Feb. 15, 2020.
Iowa Head and Neck Protocols, "Cochlear Implant (CI) Technology and Music: Music Perception, Music Enjoyment: Information for Audiologists", University of Iowa Health Care, retrieved from <https://uihealthcare.org>, last modified on Nov. 15, 2020.
Jieqing Cai et al., "A Neurophysiological Study of Musical Pitch Identification in Mandarin-Speaking Cochlear Implant Users", Neural Plasticity, vol. 2020, Article ID 4576729, retrieved from <https://doi.org/10.1155/2020/4576729>, Jul. 22, 2020.
Charlotte Prevoteau et al., "Music Enjoyment With Cochlear Implantation", Auris Nasus Larynx, vol. 45, pp. 895-902, 2018.
John S. Nemer et al. "Reduction of the Harmonic Series Influences Musical Enjoyment With Cochlear Implants", Otology & Neurotology, vol. 38, pp. 31-37, 2016.

* cited by examiner

COCHLEA ELECTRODE ARRANGEMENT, DEVICE, SYSTEM AND METHOD FOR ENHANCING MUSICAL MELODY PERCEPTION

FIELD OF THE INVENTION

The present invention relates to the field of cochlear implant, and specifically, relates to a cochlea electrode arrangement, device, system and method for enhancing musical melody perception.

BACKGROUND OF THE INVENTION

Hearing compensation or reconstruction mainly includes hearing aid selection and matching and cochlear implant. For the patients suffering from bilateral severe or extremely severe sensorineural hearing impairment, when hearing aids are used for three to six months with no obvious effects, the cochlear implant operation may be considered for reconstructing the hearing.

The cochlear implant device is a converter for simulating human cochlea functions. It converts sound signals into electrical signals via a speech processor, the electrical signals are transmitted to frequency sensing position electrodes in inner ears, the auditory nerves are directly excited in a weak stimulating manner (e.g., electricity, light, heat or mechanical pressure, etc.), and hearing is thus generated. The cochlear implant device is mainly divided into two major parts: an implant part (including a receiving device and multiple guiding electrodes) and an external part (including a sound acquisition device, a speech processor, a transmitter, etc.).

According to the auditory perception principle, the hearing refers to that outer ears acquire conducted acoustic waves, middle ears amplify acoustic wave vibration signals, then the acoustic wave vibration signals are converted into exciting signals of corresponding auditory nerves on time, frequency and strength in inner ears (i.e., cochleae) by a plurality of auditory terminal cell (also referred to as hair cell) tissues with specific frequency correspondence relationship, and the exciting signals are released and conducted by the auditory nerves and integrated in the brainstem hearing area to form auditory perception. The cochlear implant device is just a successful application of this principle. At present, the device well solves the problem of reconstructing part of the hearing ability, e.g., human speech perception, but still has some problems on enjoying and perceiving wonderful music information, and thus should be improved.

Figure 1A:
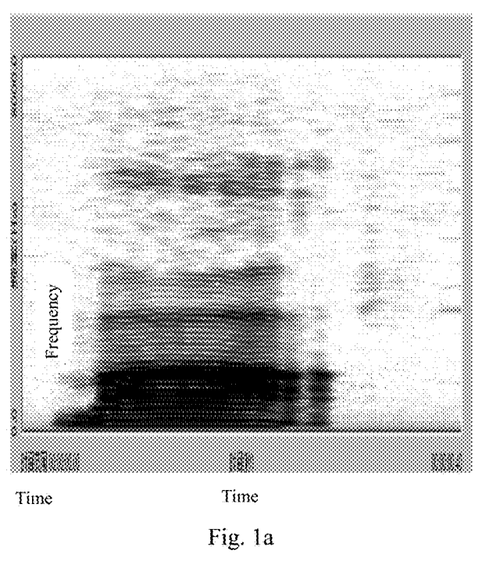
FIG. 1a shows time and frequency distribution characteristics of speech signals (na1)
Figure 1B:
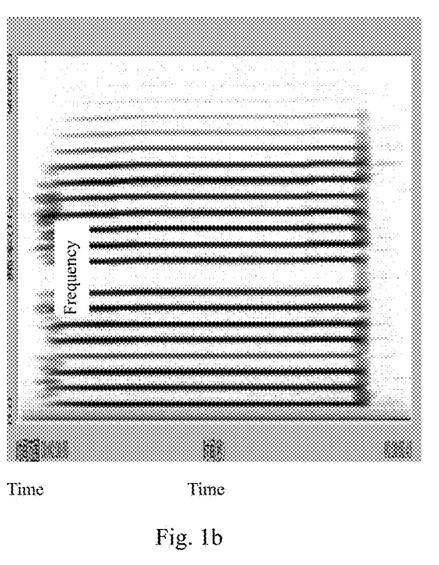
FIG. 1b shows time and frequency distribution characteristics of music signals (violin C3)

Researches discover that there is a big difference between time and frequency distribution characteristics of music signals and speech signals, as shown in FIGS. 1a and 1b. For the speech signals, the distinguishing feature of the loud part of a pronunciation word mainly lies in frequency domain envelope peak distribution, i.e., center frequency position, quantity and strength of resonance peaks of a spectrum envelop, there are often a few resonance peaks, mainly not more than five, the center frequency position of each resonance peak is indefinite, and each resonance peak has a relatively wide bandwidth (relative to the harmonic spectrum peak bandwidth of music), and includes tone information; the low unvoiced sound part in speech is also mainly displayed in a relatively wide spectrum energy concentration area, as shown by "speech" in FIG. 1a; on the time domain, the existence and speed of vocal cord vibration when a person speaks correspond to the existence and magnitude of the tone frequency, the variation range of speech is smaller than that of music and is often less than 500 Hz, but the tone frequency is changed continuously, and the time length of each distinguishing speech segment is irregular. Overall, the requirement for the resolution of main characteristic frequencies of speech signals on connected terminal auditory nerves is relatively low, the characteristic frequencies are mainly reflected at the distribution positions of resonance peaks, and how many frequency division bands are used for expressing the main sound characteristic of a speech segment is the key problem for solving speech perception. The quantity of the existing artificial ears is often not more than 22. Although the electrode array distribution of manufacturers' products is slightly different in frequency value correspondence, it is roughly based on a critical band or a frequency masking relationship. When voiced sound resonance peaks and unvoiced sound information in a speech are transmitted with such an electrode distribution, its resolution is substantially enough. However, when musical sound information is transmitted, because the spectrum structure of music signals is different from that of speech spectra, the fundamental wave frequencies of many music notes cannot be accurately conducted via auditory nerves. Table 1 gives a rough correspondence between corresponding frequency band coverage of 22 electrodes of a certain cochlear implant product and fundamental wave frequency coverage (or crossing) of notes. Thus, the existing cochlear implant patients are difficult in enjoying music information, and have poor music perception.

TABLE 1

Rough correspondence between electrode distribution of certain cochlear implant product and fundamental wave frequencies of notes

| | Band-pass filter | | Tone crossing range | |
|---|---|---|---|---|
| Electrode | center frequency | Corresponding notes | Notes | Semitone number |
| 22 | 200 | G3 | 2B~4C# | 15 |
| 21 | 360 | F4 | 4D~4A | 8 |
| 20 | 520 | C5 | 4A#~5D | 5 |
| 19 | 680 | E5 | 5D#~5F# | 4 |
| 18 | 840 | G#5 | 5G~5A | 3 |
| 17 | 1000 | C6 | 5A#~6C | 3 |
| 16 | 1160 | D6 | 6C#~6D# | 3 |
| 15 | 1327 | E6 | 6E~6F | 2 |
| 14 | 1519 | F#6 | 6F#~6G | 2 |
| 13 | 1745 | A6 | 6G#~6A# | 3 |
| 12 | 2005 | B6 | 6B~7C | 2 |
| 11 | 2304 | D7 | 7C#~7D | 2 |
| 10 | 2660 | E7 | 7D#~7F | 3 |
| 9 | 3102 | G7 | 7F#~7G# | 3 |
| 8 | 3635 | A7 | 7A~7A# | 2 |
| 7 | 4259 | C8 | 7B~8C# | 3 |
| 6 | 4990 | D#8 | 8D~8E | 3 |
| 5 | 5846 | F#8 | 8F~8G | 3 |
| 4 | 6849 | A8 | 8G#~8A | 2 |
| 3 | 8024 | B8 | 8A#~9C | 3 |

As for music sound, its sound comes from a certain musical instrument. For all the musical instruments having melodic expression, their sound levels are determined by notes, and percussion instruments having no melodic expression are not included herein. When different musical instruments play the same notes, their signal spectrum distribution is jointly formed by substantially same fundamental waves and other sub-harmonics having different amplitude distribution, the whole spectrum envelop is relatively flat, the frequency domain span is wider than that of speech, the spectrum envelop often does not have multiple obvious resonance peak changes as a speech signal spectrum envelop, but music signals have many harmonics, the harmonic order can reach dozens of times or several times according to the notes from low to high, each harmonic peak bandwidth is relatively narrow, and the peaks are spaced regularly and almost distributed according to multiple frequencies of fundamental waves, as shown by the music signal spectrogram in FIG. 1b. The fundamental wave spectrum peaks of notes are most important, and cannot be misplaced or missing, otherwise, the hearing perception of the reconstructed music signals loses the tune; for the $2^{nd}$, $3^{rd}$, $4^{th}$, $5^{th}$ . . . higher harmonic peaks corresponding to notes, if individual harmonics are missing, the melodic perception of notes is not affected, and the tune is not lost, but when many higher harmonics are missing, the tone quality will be changed obviously; and from low to high notes of a music melody, the frequency change range of fundamental waves is large from dozens of to thousands of hertz, as shown in the tone frequency table 2.1 or 2.2. In addition, on the time domain, the length of each note, namely pitch interval, is changed rhythmically, and can be controlled by signal time codes. Therefore, for cochlear implant patients, the perception of music sound is directly related to the distribution density of electrodes connected with auditory nerves.

At present, the perception of cochlear implant on music has the problems of two aspects:

1. Externally acquired and converted sound source signals should be matched with the frequency bands corresponding to cochlea electrodes, whereas this technology at present has the problem that after externally converted music signals are analyzed and filtered, when frequency band components are transmitted to the cochlea electrodes, because the existing electrode distribution positions cannot be aligned with the frequency areas where the cochleae sense music, the music frequency information is transmitted in a dislocated or lost manner, which is the main reason that the implant patients perceive music disorderly or cannot perceive music.

2. The perception on music by increasing enough electrodes in the unilateral cochlea can be theoretically realized (disclosed in the existing relevant patents at present), but excessive electrodes distributed in the unilateral cochlea will be difficult to implement on process due to the existing technical limitation.

SUMMARY OF THE INVENTION

In order to overcome the defects in the prior art, the present invention discloses a cochlea electrode arrangement, system and method for enhancing musical melody perception. With reference to the fundamental wave distribution characteristics of music notes, the frequency sensing density in a cochlea is improved by appropriately increasing electrodes, and the bilateral cochlea distribution method has the effects of ensuring process realization and improving the perception of unilateral or bilateral ears on music information.

To fulfill the above purpose, the specific solution of the present invention is as follows:

A cochlea electrode arrangement for enhancing musical melody perception, nearby a cochlear basilar membrane on each side, according to the characteristic frequency correspondence of music notes, a phonosensitive full spectrum band corresponding to the cochlea apex to cochlea base is divided into frequency areas in response to specific notes; a conducting or stimulating electrode for frequency band signals is placed in each frequency area, namely each electrode is placed in the characteristic frequency band where the music notes are located, the electrodes are divided into two groups, two electrode distribution methods, namely an equalization method and a main-auxiliary method, are adopted for bilateral ears by using the characteristic of dual ears and dual tracks, a corresponding group of electrodes is implanted into the cochleae on two sides respectively, and each electrode roughly corresponds to the fundamental wave frequency point of a different note.

Furthermore, for the equalization method, the same number of electrodes are implanted into the bilateral cochleae respectively, and grouped into electrode arrays in an equal-pitch interval alternating manner at set frequency bands.

Furthermore, excessive electrodes should not be arranged in the low frequency area due to small very low note frequency intervals, meanwhile, a few very low notes are used, so a few representative frequency points are selected and respectively arranged at corresponding positions nearby the bilateral cochlea apexes, e.g., three electrodes marked nearby the low frequency area in table 2.1.

Further, 33 electrodes are respectively implanted into the remaining frequency areas in the bilateral cochleae except the low frequency areas;

on one side, the arrangement of electrodes implanted into the cochlea is:

the $1^{st}$ electrode corresponds to the fundamental wave frequency of a B8 note; the $33^{rd}$ electrode corresponds to the fundamental wave frequency of a G3 note, and the electrodes between the $1^{st}$ electrode and the $33^{rd}$ electrode are arranged according to a whole-tone frequency interval;

Further, the three electrodes in the low frequency area are respectively: the $36^{th}$ electrode corresponds to the fundamental wave frequency of an A1 note, the $35^{th}$ electrode corresponds to the fundamental wave frequency of an E2 note, and the $34^{th}$ electrode corresponds to the fundamental wave frequency of a C3 note.

The arrangement of 33 electrodes implanted into the remaining frequency areas of the cochlea on the other side except the low frequency area is:

the $1^{st}$ electrode corresponds to the fundamental wave frequency of a C9 note; the $33^{rd}$ electrode corresponds to the fundamental wave frequency of a G#/Ab3 note, and the electrodes between the $1^{st}$ electrode and the $33^{rd}$ electrode are also arranged according to a whole-tone note frequency interval.

As for the main-auxiliary method, different numbers of electrodes are implanted into the bilateral cochleae respectively, and grouped into electrode arrays in a specified frequency interval alternating manner at set frequency bands.

Further, at the low frequency area, corresponding representative frequency points are selected for arranging corresponding electrodes, the electrodes are respectively implanted into the bilateral cochleae, and three identical electrodes are distributed on two sides respectively.

Further, when different numbers of electrodes are implanted into the bilateral cochleae respectively, a "main electrode group", totally 38 electrodes, is distributed in correspondence to the main frequency sensing area of the cochlea on one side, and an "auxiliary electrode group", totally 27 electrodes, is distributed in correspondence to the main frequency sensing area of the cochlea on the other side.

The arrangement of the main electrode group distributed in one cochlea is: the $1^{st}$ electrode corresponds to the fundamental wave frequency of the B8 note; the $38^{th}$ electrode corresponds to the fundamental wave frequency of the G3 note, and the electrodes between the 1$^{st}$ electrode and the 38$^{th}$ electrode are arranged according to the note frequency correspondence in a set manner;

The arrangement of the auxiliary electrode group implanted into the other cochlea is: the 1$^{st}$ electrode corresponds to the fundamental wave frequency of an A#/Bb8 note; the 27$^{th}$ electrode corresponds to the fundamental wave frequency of the G#/Ab3 note, and the electrodes between the 1$^{st}$ electrode and the 27$^{th}$ electrode are also arranged according to the note frequency correspondence in a set manner.

Further, in the low frequency areas, the three electrodes are respectively: in the main electrode group, the 41$^{st}$ electrode corresponds to the fundamental wave frequency of the A1 note, the 40$^{th}$ electrode corresponds to the fundamental wave frequency of the E2 note, and the 39$^{th}$ electrode corresponds to the fundamental wave frequency of the C3 note; and in the auxiliary electrode group, the 30$^{th}$ electrode corresponds to the fundamental wave frequency of the A1 note, the 29$^{th}$ electrode corresponds to the fundamental wave frequency of the E2 note, and the 28$^{th}$ electrode corresponds to the fundamental wave frequency of the C3 note.

A cochlea electrode arrangement method for enhancing musical melody perception, including the following steps:

dividing electrodes into two groups, and implanting a corresponding group of electrodes into bilateral cochleae respectively, wherein each electrode is arranged in a corresponding characteristic frequency band where music notes are located, the electrodes are mainly concentrated in main frequency sensing areas of 100 Hz-8000 Hz, and corresponding representative frequency points are selected for arranging the electrodes in low frequency areas;

wherein for an equalization method, when the electrodes are divided into two groups of the same number, the electrodes are arranged in a left-right staggered and equal interval manner in the unilateral cochlea according to fundamental wave characteristic frequencies of notes in the main frequency sensing area; and in a main-auxiliary method, when the electrodes are divided into two groups of unequal numbers, the electrodes are arranged in the unilateral cochlea according to fundamental wave characteristic frequencies of notes in a set manner.

A cochlea electrode array device for enhancing musical melody perception, including a plurality of electrodes, wherein each electrode includes a plurality of annular electrode contacts, the annular electrode contacts are all connected with electrode circuits via metal wires with insulating layers, the electrode further includes a flexible envelope wrapping all the electrode circuits, and the electrodes are arranged into arrays according to said electrode arrangement method. The electrode array device may also adopt a special material structure for conducting light or heat or pressure besides the said conductive material, corresponding to said electrode arrangement method.

In order to better implement said electrode arrangement method of the present invention, the present invention further discloses an cochlear implant system for enhancing musical melody perception, including an implant part and an external part, wherein the implant part and the external part may adopt a wireless communication connection mode or a wired connection mode, the implant part at least includes an electrode array device, the external part at least includes a sound processor and a sound acquisition device connected with the processor, sound signals are acquired by the sound acquisition device, notes and pitch intervals of a main melody of music signals are analyzed and coded by the processor, corresponding MIDI music codes are generated by the processor according to the type of a musical instrument and converted into bilateral cochlea electrode stimulating coded signals via a corresponding processing algorithm, and the stimulating coded signals are transmitted to stimulated parts via wireless communication or dedicated wired interface drive.

Further, for the wireless communication connection mode, the electrode array device and a receiving device serve as the implant part of an cochlear implant, and a transmitter, the processor and the sound acquisition device serve as the external part of the cochlear implant.

Further, for the wired connection mode, the electrode array device serves as the implant part of an cochlear implant, a wired interface device, a signal drive device, the processor and the sound acquisition device serve as the external part, signals acquired by the sound acquisition device are transmitted to the processor, the processor decomposes and quantifies the obtained signals to generate corresponding signals and transmits the signals to the signal drive device, the signal drive device transits each path of signals generated by drive to the wired interface device, and each path of signals is connected with each path of signals of implanted electrodes at the wired interface device to generate corresponding stimulating signals.

Further, the wireless communication mode of the implant part and the external part may be a Bluetooth communication mode, an infrared communication mode or a radio frequency (RF) communication mode, and the wired connection mode may be a connection structure wrapped by a flexible material; and the connection structure may be an optical connection structure, a thermal connection structure or a mechanical connection structure.

A working method of the cochlear implant system for enhancing musical melody perception, including the following steps:

signals acquired by a sound acquisition device are transmitted to a processor, and the processor analyzes and encodes notes and pitch intervals of a main melody of the music signals, wherein the processor can generate corresponding MIDI music codes according to the type of a musical instrument, and processes the codes via a processing algorithm corresponding to a mode;

the processor determines the location of an effective working electrode of each note according to the electrode working mode, and determines an array on each side and each electrode coding sequence;

the processor converts the music codes into bilateral cochlea electrode stimulating coded signals via the processing algorithm corresponding to the mode, and the stimulating coded signals are transmitted to stimulated parts via wireless communication or dedicated wired interface drive.

The present invention has the following beneficial effects:

The present invention gives a bilateral cochlea implant electrode arrangement method, electrode arrays are arranged at dual ears according to note characteristic frequency semitone division at the most commonly used bands (about 100 Hz-8000 Hz) of musical sound and speech by equal pitch interval alternation (i.e., an equalization method) method or specified frequency alternation (i.e., a main-auxiliary method) grouping, and only representative frequency points are selected for a low frequency area of which the spatial size does not allow excessive frequency points, and distributed in the electrode array(s) on the main side or two sides to reconstruct and enhance music and speech perception; in the present invention, electrodes are arranged at bilateral cochleae, which is easy to realize over unilateral cochlea distribution of so many electrodes, and this electrode distribution method can be used unilaterally or bilaterally, so that implanted patients can perceive music better with the use of binaural phonosensitive superimposed effect.

Since the distribution of musical sound frequency point placeholders is considered in the optimized electrode distribution, the electrode density is improved at the unilateral cochlea, and the music perception can be enhanced; meanwhile, the method covers original speech electrode frequency points, so even if the electrodes on any side work, the speech perception produced by the method can be guaranteed to be not lower than that obtained by the present electrode distribution method by selection and handover of the working mode of an external sound processor and a sound coding strategy. Therefore, the present invention has practical significance for enhancing cochlear implant perception on richer music sound.

DETAILED DESCRIPTION OF THE EMBODIMENTS

The present invention will be specified below in combination with the accompanying drawings.

Hair cells (i.e., auditory cells) on the basilar membrane of a cochlea having the function of analyzing or sensing frequency components are connected with terminal auditory nerves, and their topological locations in the cochlea correspond to the frequency components. If the perception of music is desired to be accurately reconstructed in the cerebral hearing area, so that an cochlear implant patient can feel wonderful musical melody, electrodes should be added to connect the corresponding auditory nerves. However, excessive electrodes are difficult to be implanted in the unilateral cochlea, thus, the present invention utilizes the fact that human ears have bilateral cochleae and the dual ears have a superposed sensing effect, frequency values are selected by means of an equalization method and a main-auxiliary method, and stimulating electrodes are distributed at the topological locations in the corresponding cochleae to connect the terminal auditory nerves.

Table 2.1 is a corresponding schematic table of note frequencies in an equalization method, in bilateral arrangement, the note frequencies corresponding to medium and high frequency electrodes on one side are bold, the note frequencies corresponding to medium and high frequency electrodes on the other side are italic, and the note frequencies corresponding to common electrodes arranged at the low frequency parts are bold and underlined.

In the equalization method, when bilateral electrodes are arranged specifically, the specific relations between the electrodes and the note frequencies are shown in table 3.1 and table 3.2.

Table 2.2 is a corresponding schematic table of note frequencies in a main-auxiliary method, wherein the note frequencies corresponding to medium and high frequency electrodes in the main side are bold; the note frequencies corresponding to medium and high frequency electrodes in the auxiliary side are italic; and the note frequencies corresponding to common electrodes arranged at the low frequency parts are bold and underlined.

In the main-auxiliary method, when electrodes in the main and auxiliary sides are arranged specifically, the specific relationship between the electrodes and the note frequencies are shown in table 3.3 and table 3.4.

TABLE 2.1

Corresponding table of note frequencies in equalization method (one side: bold; the other side: italic; low frequency common: bold + underlined)

| Note | Deg. 8 | | | | | | | | | |
|------|---|---|---|---|---|---|---|---|---|---|
|      | 0 | 1 | 2 | 3 | 4 | 5 | 6 | 7 | 8 | 9 |
| C     | 16.352 | 32.703 | 65.406 | <u>130.81</u> | 261.63 | 523.25 | *1046.5* | *2093.0* | 4186.0 | 8372.0 |
| C#/Db | 17.324 | 34.648 | 69.296 | 138.59 | *277.18* | *544.37* | *1108.7* | *2217.5* | *4434.9* | 8869.8 |
| D     | 18.354 | 36.708 | 73.416 | 146.83 | 293.66 | 587.33 | 1174.7 | 2349.3 | 4698.6 | 9397.3 |
| D#/Eb | 19.445 | 38.891 | 77.782 | 155.56 | *311.13* | *622.25* | *1244.5* | *2489.0* | *4978.0* | 9956.1 |
| E     | 20.60 | 41.20 | <u>82.407</u> | 164.8 | 329.6 | 659.2 | 1318.5 | 2637.0 | 5274.0 | 10548 |
| F     | 21.827 | 43.654 | 87.307 | 174.61 | *349.23* | *698.46* | *1396.9* | *2793.8* | *5587.7* | 11175 |
| F#/Eb | 23.125 | 46.249 | 92.449 | 185.00 | 369.99 | 739.99 | 1480.0 | 2960.0 | 5919.9 | 11840 |
| G     | 24.500 | 48.999 | 97.999 | *196.00* | *392.00* | *783.99* | *1568.0* | *3136.0* | *6271.9* | 12544 |
| G#/Ab | 25.957 | 51.913 | 103.83 | 207.65 | 415.30 | 830.61 | 1661.2 | 3322.4 | 6644.9 | 13290 |
| A     | 27.500 | <u>55.000</u> | 110.00 | *220.00* | *440.00* | *880.00* | *1760.0* | *3520.0* | *7040.0* | 14080 |
| A#/Bb | 29.135 | 58.270 | 116.54 | 233.08 | 466.16 | 932.33 | 1864.7 | 3729.3 | 7458.6 | 14917 |
| B     | 30.868 | 61.735 | 123.47 | 246.94 | *493.88* | *987.77* | *1975.5* | *3951.1* | *7902.1* | 15804 |

TABLE 2.2

Corresponding table of note frequencies in main-auxiliary method (main side: bold; auxiliary side: italic; low frequency common: bold + underlined)

| Note | Deg. 8 | | | | | | | | | |
|---|---|---|---|---|---|---|---|---|---|---|
| | 0 | 1 | 2 | 3 | 4 | 5 | 6 | 7 | 8 | 9 |
| C | 16.352 | 32.703 | 65.406 | 130.81 | 261.63 | 523.25 | 1046.5 | 2093.0 | 4186.0 | 8372.0 |
| C#/Db | 17.324 | 34.648 | 69.296 | 138.59 | *277.18* | *544.37* | *1108.7* | *2217.5* | *4434.9* | *8869.8* |
| D | 18.354 | 36.708 | 73.416 | 146.83 | 293.66 | 587.33 | 1174.7 | 2349.3 | 4698.6 | 9397.3 |
| D#/Eb | 19.445 | 38.891 | 77.782 | 155.56 | *311.13* | *622.25* | *1244.5* | *2459.0* | *4978.0* | *9956.1* |
| E | 20.60 | 41.20 | 82.407 | 164.8 | 329.6 | 659.2 | 1318.5 | 2637.0 | 5274.0 | 10548 |
| F | 21.827 | 43.654 | 87.307 | 174.61 | *349.23* | *698.46* | *1396.9* | *2793.8* | *5587.7* | 11175 |
| F#/Eb | 23.125 | 46.249 | 92.449 | 185.00 | *369.99* | *739.99* | *1480.0* | *2960.0* | *5919.9* | 11840 |
| G | 24.500 | 48.999 | 97.999 | 196.00 | 392.00 | 783.99 | 1568.0 | 3136.0 | 6271.9 | 12544 |
| G#/Ab | 25.957 | 51.913 | 103.83 | *207.65* | *415.30* | *830.61* | *1661.2* | *3322.4* | *6644.9* | 13290 |
| A | 27.500 | 55.000 | 110.00 | 220.00 | 440.00 | 880.00 | 1760.0 | 3520.0 | 7040.0 | 14080 |
| A#/Bb | 29.135 | 58.270 | 116.54 | *233.08* | *466.16* | *932.33* | *1864.7* | *3729.3* | *7458.6* | 14917 |
| B | 30.868 | 61.735 | 123.47 | 246.94 | 493.88 | 987.77 | 1975.5 | 3951.1 | 7902.1 | 15804 |

TABLE 3.1

Electrode distribution on one side in bilateral equalization method

| No. | Note | Center frequency | Pass band range |
|---|---|---|---|
| 36 | A1 | 55 | 52.6-57.4 |
| 35 | E2 | 82.407 | 80.0-84.8 |
| 34 | C3 | 130.8 | 127.1-134.5 |
| 32 | G#/Ab3 | 207.65 | 201.7-213.6 |
| 31 | A#/Bb3 | 233.08 | 226.4-239.8 |
| 30 | C4 | 261.63 | 254.1-261.1 |
| 29 | D4 | 293.66 | 285.2-302.1 |
| 28 | E4 | 329.6 | 320.2-339.1 |
| 27 | F#/Eb4 | 369.99 | 359.4-380.6 |
| 26 | G#/Ab4 | 415.3 | 403.4-427.2 |
| 25 | A#/Bb4 | 466.16 | 452.8-479.5 |
| 24 | C5 | 523.25 | 508.2-538.3 |
| 23 | D5 | 587.33 | 570.5-604.1 |
| 22 | E5 | 659.2 | 640.5-678.1 |
| 21 | F#/Eb5 | 739.99 | 718.9-761.1 |
| 20 | G#/Ab5 | 830.61 | 806.9-854.3 |
| 19 | A#/Bb5 | 932.33 | 905.7-958.9 |
| 18 | C6 | 1046.5 | 1016.7-1076.3 |
| 17 | D6 | 1174.7 | 1141.1-1208.3 |
| 16 | E6 | 1318.5 | 1280.7-1356.3 |
| 15 | F#/Eb6 | 1480.00 | 1437.5-1522.5 |
| 14 | G#/Ab6 | 1661.2 | 1613.5-1708.9 |
| 13 | A#/Bb6 | 1864.7 | 1811.1-1918.3 |
| 12 | C7 | 2093 | 2032.7-3045.3 |
| 11 | D7 | 2349.3 | 2281.7-2416.9 |
| 10 | E7 | 2637 | 2561.1-2712.9 |
| 9 | F#/Eb7 | 2960 | 2874.7-3045.3 |
| 8 | G#/Ab7 | 3322.4 | 3226.7-3418.1 |
| 7 | A#/Bb7 | 3729.3 | 3621.9-3836.7 |
| 6 | C8 | 4186 | 4065.5-4306.5 |
| 5 | D8 | 4698.6 | 4563.3-4833.9 |
| 4 | E8 | 5274 | 5122.1-5425.9 |
| 3 | F#/Eb8 | 5919.9 | 5749.5-6090.3 |
| 2 | G#/Ab8 | 6644.9 | 6454-6835.8 |
| 1 | A#/Bb8 | 7458.6 | 7245.1-7672.1 |

TABLE 3.2

Electrode distribution on the other side in bilateral equalization method

| No. | Note | Center frequency | Pass band range |
|---|---|---|---|
| 36 | A1 | 55 | 52.6-57.4 |
| 35 | E2 | 82.407 | 80.0-84.8 |
| 34 | C3 | 130.8 | 127.1-134.5 |
| 33 | G3 | 196.00 | 190.3-201.7 |
| 32 | A3 | 220.00 | 213.6-226.4 |
| 31 | B3 | 246.94 | 239.8-254.1 |
| 30 | C#/Db4 | 277.18 | 269.1-285.2 |
| 29 | D#/Eb4 | 311.13 | 302.1-320.2 |
| 28 | F4 | 349.23 | 339.1-359.4 |
| 27 | G4 | 392.00 | 380.6-403.4 |
| 26 | A4 | 440.00 | 427.2-452.8 |
| 25 | B4 | 493.88 | 479.5-508.2 |
| 24 | C#/Db5 | 544.37 | 538.5-570.5 |
| 23 | D#/Eb5 | 622.25 | 604.1-640.5 |
| 22 | F5 | 698.46 | 678.1-718.9 |
| 21 | G5 | 783.99 | 761.1-806.9 |
| 20 | A5 | 880.00 | 854.3-905.7 |
| 19 | B5 | 987.77 | 958.9-1016.7 |
| 18 | C#/Db6 | 1108.70 | 1076.3-1141.1 |
| 17 | D#/Eb6 | 1244.50 | 1208.3-1280.7 |
| 16 | F6 | 1396.90 | 1356.3-1437.5 |
| 15 | G6 | 1568.00 | 1522.5-1613.5 |
| 14 | A6 | 1760.00 | 1708.9-1811.1 |
| 13 | B6 | 1975.50 | 1918.3-2032.7 |
| 12 | C#/Db7 | 2217.50 | 2153.3-2281.7 |
| 11 | D#/Eb7 | 2489.00 | 2416.9-2561.1 |
| 10 | F7 | 2793.80 | 2712.9-2874.7 |
| 9 | G7 | 3136.00 | 3045.3-3226.7 |
| 8 | A7 | 3520.00 | 3418.1-3621.9 |
| 7 | B7 | 3951.10 | 3836.7-4065.5 |
| 6 | C#/Db8 | 4434.90 | 4306.5-4563.3 |
| 5 | D#/Eb8 | 4978.00 | 4833.9-5122.1 |
| 4 | F8 | 5587.70 | 5425.9-5749.5 |
| 3 | G8 | 6271.90 | 6090.1-6453.7 |
| 2 | A8 | 7040.00 | 6835.7-7244.3 |
| 1 | B8 | 7902.10 | 7672.8-8131.4 |

TABLE 3.3

Electrode distribution on main side in main-auxiliary method

| No. | Note | Center frequency | Pass band range |
|---|---|---|---|
| 41 | A1 | 55 | 52.6-57.4 |
| 40 | E2 | 82.407 | 80.0-84.8 |
| 39 | C3 | 130.8 | 127.1-134.5 |
| 38 | G3 | 196.00 | 190.3-201.7 |
| 37 | A3 | 220.00 | 213.6-226.4 |

TABLE 3.3-continued

Electrode distribution on main side in main-auxiliary method

| No. | Note | Center frequency | Pass band range |
|---|---|---|---|
| 36 | B3 | 246.94 | 239.8-254.1 |
| 35 | C4 | 261.63 | 254.1-261.1 |
| 34 | D4 | 293.66 | 285.2-302.1 |
| 33 | E4 | 329.6 | 320.2-339.1 |
| 32 | F4 | 349.23 | 339.1-359.4 |
| 31 | G4 | 392.00 | 380.6-403.4 |
| 30 | A4 | 440.00 | 427.2-452.8 |
| 29 | B4 | 493.88 | 479.5-508.2 |
| 28 | C5 | 523.25 | 508.2-538.3 |
| 27 | D5 | 587.33 | 570.5-604.1 |
| 26 | E5 | 659.2 | 640.5-678.1 |
| 25 | F5 | 698.46 | 678.1-718.9 |
| 24 | G5 | 783.99 | 761.1-806.9 |
| 23 | A5 | 880.00 | 854.3-905.7 |
| 22 | B5 | 987.77 | 958.9-1016.7 |
| 21 | C6 | 1046.5 | 1016.7-1076.3 |
| 20 | D6 | 1174.7 | 1141.1-1208.3 |
| 19 | E6 | 1318.5 | 1280.7-1356.3 |
| 18 | F6 | 1396.90 | 1356.3-1437.5 |
| 17 | G6 | 1568.00 | 1522.5-1613.5 |
| 16 | A6 | 1760.00 | 1708.9-1811.1 |
| 15 | B6 | 1975.50 | 1918.3-2032.7 |
| 14 | C7 | 2093 | 2032.7-3045.3 |
| 13 | D7 | 2349.3 | 2281.7-2416.9 |
| 12 | E7 | 2637 | 2561.1-2712.9 |
| 11 | F7 | 2793.80 | 2712.9-2874.7 |
| 10 | G7 | 3136.00 | 3045.3-3226.7 |
| 9 | A7 | 3520.00 | 3418.1-3621.9 |
| 8 | B7 | 3951.10 | 3836.7-4065.5 |
| 7 | C8 | 4186 | 4065.5-4306.5 |
| 6 | D8 | 4698.6 | 4563.3-4833.9 |
| 5 | E8 | 5274 | 5122.1-5425.9 |
| 4 | F8 | 5587.70 | 5425.9-5749.5 |
| 3 | G8 | 6271.90 | 6090.1-6453.7 |
| 2 | A8 | 7040.00 | 6835.7-7244.3 |
| 1 | B8 | 7902.10 | 7672.8-8131.4 |

TABLE 3.4

Electrode distribution on auxiliary side in main-auxiliary method

| No. | Note | Center frequency | Pass band range |
|---|---|---|---|
| 27 | G#/Ab3 | 207.65 | 201.7-213.6 |
| 26 | A#/Bb3 | 233.08 | 226.4-239.8 |
| 25 | C#/Db4 | 277.18 | 269.1-285.2 |
| 24 | D#/Eb4 | 311.13 | 302.1-320.2 |
| 23 | F#/Eb4 | 369.99 | 359.4-380.6 |
| 22 | G#/Ab4 | 415.3 | 403.4-427.2 |
| 21 | A#/Bb4 | 466.16 | 452.8-479.5 |
| 20 | C#/Db5 | 544.37 | 538.3-570.5 |
| 19 | D#/Eb5 | 622.25 | 604.1-640.5 |
| 18 | F#/Eb5 | 739.99 | 718.9-761.1 |
| 17 | G#/Ab5 | 830.61 | 806.9-854.3 |
| 16 | A#/Bb5 | 932.33 | 905.7-958.9 |
| 15 | C#/Db6 | 1108.70 | 1076.3-1141.1 |
| 14 | D#/Eb6 | 1244.50 | 1208.3-1280.7 |
| 13 | F#/Eb6 | 1480.00 | 1437.5-1522.5 |
| 12 | G#/Ab6 | 1661.2 | 1613.5-1708.9 |
| 11 | A#/Bb6 | 1864.7 | 1811.1-1918.3 |
| 10 | C#/Db7 | 2217.50 | 2153.3-2281.7 |
| 9 | D#/Eb7 | 2489.00 | 2416.9-2561.1 |
| 8 | F#/Eb7 | 2960 | 2874.7-3045.3 |
| 7 | G#/Ab7 | 3322.4 | 3226.7-3418.1 |
| 6 | A#/Bb7 | 3729.3 | 3621.9-3836.7 |
| 5 | C#/Db8 | 4434.90 | 4306.5-4563.3 |
| 4 | D#/Eb8 | 4978.00 | 4833.9-5122.1 |
| 3 | F#/Eb8 | 5919.9 | 5749.5-6090.3 |
| 2 | G#/Ab8 | 6644.9 | 6454-6835.8 |
| 1 | A#/Bb8 | 7458.6 | 7245.1-7672.1 |

Figure 2A:
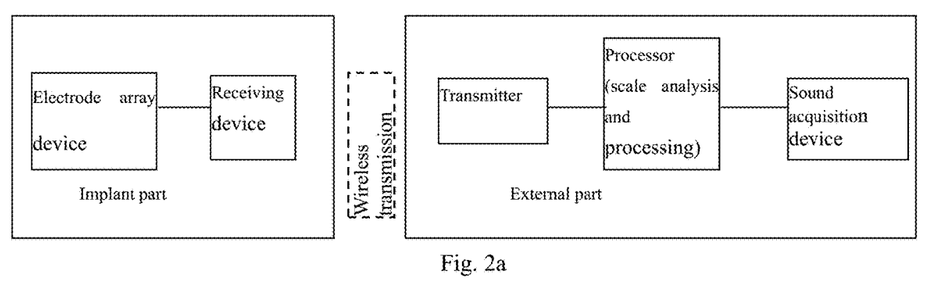
FIG. 2a is a structural block diagram of a unilateral or bilateral cochlear implant system in a wireless transmission mode.
Figure 2B:
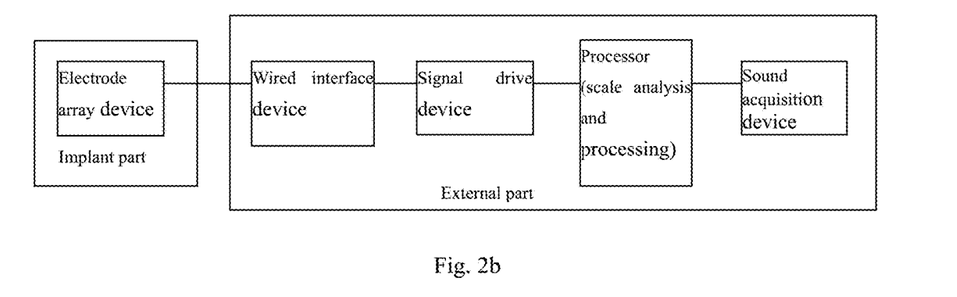
FIG. 2b is a structural block diagram of a unilateral or bilateral cochlear implant system in a wired connection mode.

As shown in FIGS. 2a and 2b, when the present invention is implemented, electrodes are used in an cochlear implant system which includes an implant part and an external part, wherein the implant part includes an electrode array device arranged according to the above-mentioned mode; when the implant part is in wireless communication with the external part, the electrode array device is connected with a receiving device; and the external part includes a transmitter, a processor and a sound acquisition device connected in sequence. The sound acquisition device transmits the acquired signals to the processor, the processor transmits the signals to the transmitter after further processing, the transmitter transmits the processed signals to the receiving device wirelessly, the receiving device triggers the actions of the electrodes according to the received signals, and the corresponding electrodes act so that human ears can hear corresponding music signals.

When the implant part is in wired communication with the external part, the electrode array device serves as an implant part, and the external part includes a wired interface device, a signal drive device, a processor and a sound acquisition device connected in sequence. The sound acquisition device transmits the acquired signals to the processor, the processor transmits the signals to the signal drive device after further processing, the signal drive device transmits the processed signals to the electrode array device via the wired interface device, the electrode array device triggers the actions of the electrodes according to the received signals, and the corresponding electrodes act so that human ears can hear corresponding music signals.

The processor outside the ear can convert music signals into MIDI coded data of music by analyzing the music signals, and the data of this format can drive stimulating signals of each path of corresponding electrodes. Obviously, the electrodes distributed more closely can accurately correspond to the frequency points of music notes so that an cochlear implant patient can accurately acquire notes and harmonic information, moreover, speech characteristic frequencies can be transmitted by determining working electrodes from closer electrodes according to the principle of proximity mapping and adopting a speech processing coding strategy correspondingly, therefore, the electrode arrangement method and system consider the transmission of speech information and do not affect speech perception. However, if a few original electrodes are adopted for mapping transmission of music notes, even if the external sound processor accurately analyzes the music note information, the internal cochlea electrode cannot accurately correspond to the frequency points or connect the auditory nerves to transmit the music note information to the brain, and the music perception is still lacking. This also explains why the existing cochlear implant cannot well perceive music.

Experimental studies further discover that human ears have binaural phonosensitive superposition characteristic, and this characteristic is not only beneficial to distinguishing a sound source and improving the orientation capability of the sound source, but also can integrate sound effects of the brain stem area, i.e., can increase the volume of sound and superpose musical melody and harmonic information.

Figure 3:
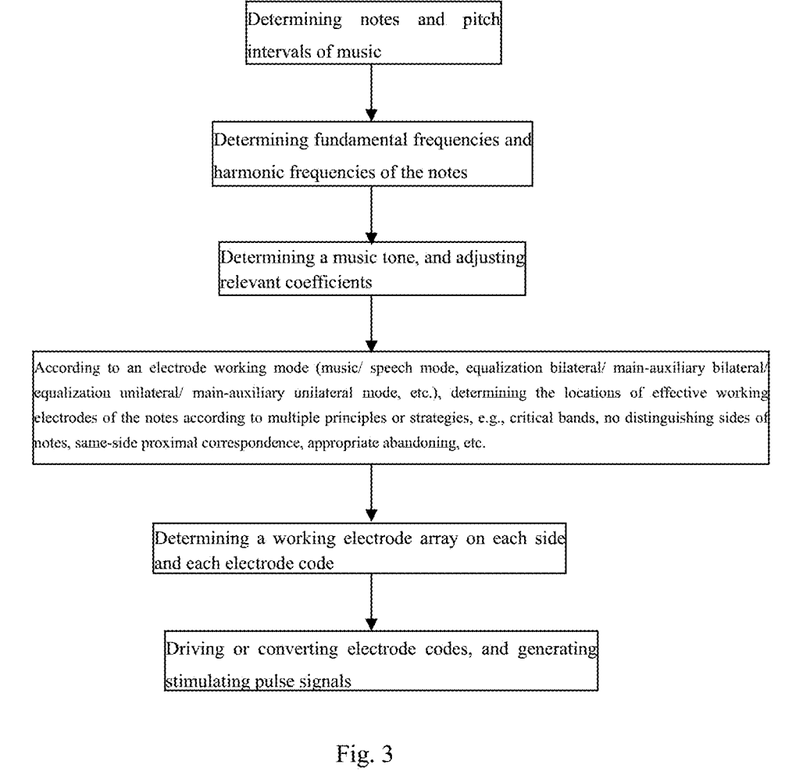
FIG. 3 is a block diagram of a signal processing flow of an electrode system on each side.
Figure 4:
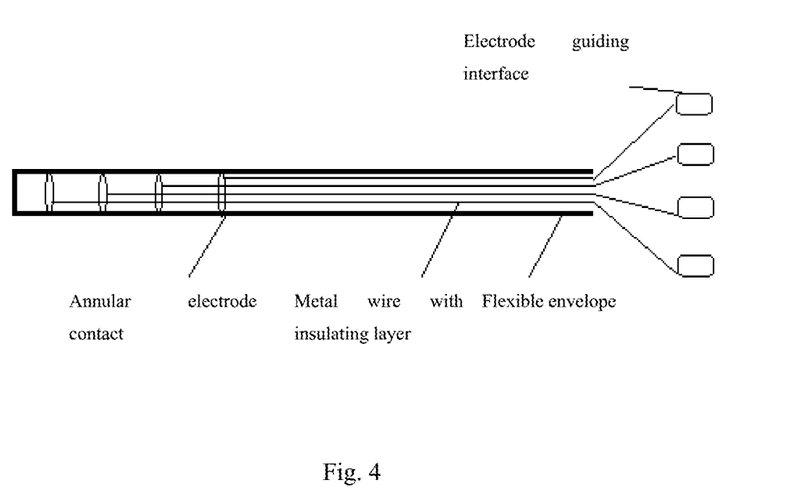
FIG. 4 is a structural schematic diagram of an electrode array on each side.

The signal processing flow of electrodes on each side in the cochlear implant system is as shown in FIG. 3:

Step 1: determining notes and pitch intervals (similar to MIDI coded information) of music;

Step 2: determining fundamental frequencies and harmonic frequencies of the notes;

Step 3: determining a music tone, and adjusting relevant coefficients;

Step 4: according to an electrode working mode including an equalization bilateral mode, a main-auxiliary bilateral mode, an equalization unilateral mode, a main-auxiliary unilateral mode, a music mode/speech mode and the like, determining the locations of effective working electrodes of the notes according to multiple principles or strategies, e.g., critical bands, no distinguishing sides of notes, same-side proximal correspondence, appropriate abandoning, etc.;

Step 5: determining working electrode locations on each side and the signal coding sequence of each electrode;

Step 6: driving or converting electrode codes, and generating stimulating pulse signals.

Figure 5:
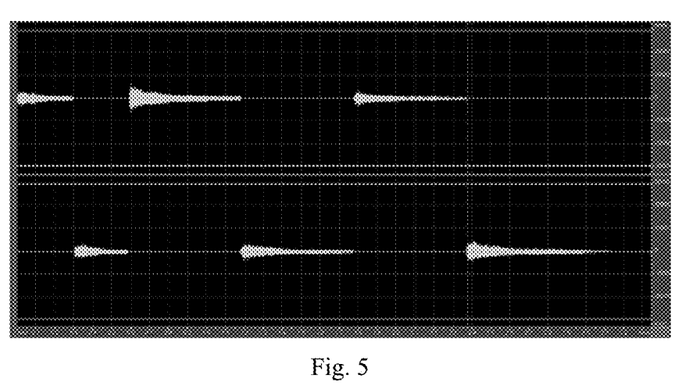
FIG. 5 shows waveforms of binaural superposed musical sound simulation synthetic signals.

In this embodiment, for the multi-channel superposed sensing effect of musical melody, we made special simulation analysis, supposing that the optimal restoration effect of cochlear implant can reach normal human binaural perception, so we adopted normal human ears for simulation. As shown in FIG. 5, the upper and lower waveforms are respectively time domain waveforms of sound signals heard by left and right track cochleae, wherein the upper left track waveform shows simulated sound synthesized by left ear electrodes, including synthetic sound signals of fundamental waves and main harmonics of corresponding notes; and the lower right track waveform shows simulated sound synthesized by right ear electrodes, including synthetic sound signals of fundamental waves and main harmonics of corresponding notes. Thus, the music heard at the cerebral hearing area alternatively transmit and synthesizing by left and right tracks, and its melodic perception on segments is complete and accurate.

Experimental results show that the dual track technology can transmit more sub-band characteristics of music signals, and can transmit fundamental wave and key harmonic components more accurately and conveniently, thus increasing the electrode number of cochlear implant in other ways.

The tone of music notes is mainly determined by fundamental wave frequencies, while the timbre of tones is determined according to spectrum characteristics, i.e., determined by the ratio of fundamental waves to harmonics and the quantity of harmonics. The electrode arrangement solution of this patent just shows that the fundamental wave frequencies needed by all the music note expressions are firstly distributed well and then divided into two groups for bilateral arrangement to reduce the number of unilateral electrodes and lower the arrangement difficulty, and then the fundamental wave and harmonic frequencies of a certain note which needs to be expressed are mapped to an electrode array on one side according to a certain principle, thus ensuring that the same note works at the electrodes on one side and different notes can be expressed at the electrode arrays on different sides, and then realizing that the whole music segment adopts a melody processing strategy of bilaterally and alternatively synthesizing the sound effect. In actual corresponding conversion and expression, the center frequencies of a few harmonics may proximally fall onto the electrode locations on the other side, and this situation may be handled by adopting the principle of same-side proximity or appropriate abandoning.

In order to illustrate the effects achieved by the electrode arrangement mode of the present invention better, the present invention gives another embodiment:

Based on the above-mentioned dual track cochlea electrode arrangement method, the cochlear implant music sound processor generates corresponding electrode stimulating signals according to the electrode working mode and coding strategy and the signal processing flow of FIG. 3, wherein if the notes are lower, there are more harmonics in the music perception frequency band range and more corresponding stimulating electrodes; and if the notes are higher, there are less harmonics and less effective stimulating electrodes. When each note working electrode is determined, each effective working electrode, i.e., each electrode in the same-side cochlea where fundamental waves and effective harmonics are accurately or in approximate correspondence, is determined according to the principle of critical bands, wherein individual harmonics may be abandoned, e.g., the harmonics approximated to the electrodes on the other side. This analysis and processing operation is completed by the external sound processor.

For different musical instruments, the amplitude ratio relationships of harmonic components thereof are different, so parameters are often adjusted appropriately according to the type of a musical instrument.

Figure 6:
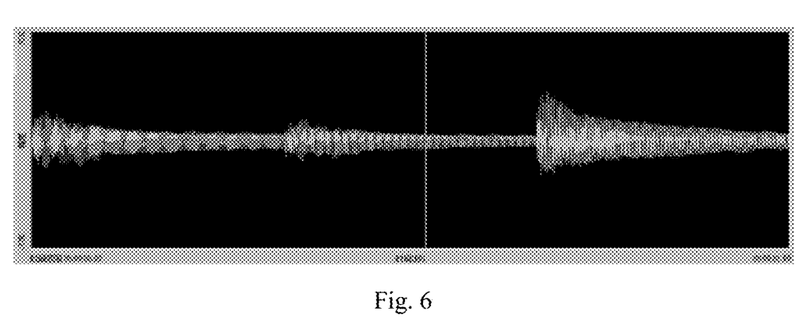
FIG. 6 is a waveform diagram corresponding to a section of musical melody in one embodiment.

The working condition of electrodes will be illustrated, taking a simple melody as an example:

A musical melody composed of three notes A3, G3 and C4 is selected, the note intervals are supposed to be equal, and the signal waveform is shown in FIG. 6.

Fundamental waves of the notes are determined at first, and then alternative electrodes of the fundamental waves and harmonics of the notes are allocated according to the processing flow of FIG. 3 and the coding strategy (i.e., critical band limitation, determining working electrodes on the basis that the harmonics of the same note are on the same side, abandoning the electrodes corresponding to the harmonics on different sides, etc.), as shown in tables 4.1, 4.2 and 4.3, to stimulate the auditory nerve system, thereby ensuring that music signals of the same note on random sides are connected to auditory nerves for stimulating, without destroying the integrity of note perception. In this case, each working electrode is determined on one side for each note, different notes may work on the same side or work alternately on different sides, and the complete musical melody is perceived by the superposition effect that the bilateral cochlea electrode arrays stimulate the auditory nerves.

If in a bilateral equalized electrode mode, for a melody section A3, G3 and C4, the $1^{st}$ and $2^{nd}$ notes work on the electrodes of one side, while the $3^{rd}$ note works on the electrodes of the other side, e.g., table 4.1 gives an electrode condition that the $1^{st}$ (A3) and $2^{nd}$ (G3) notes work in sequence on one side, and table 4.2 gives a working condition of electrodes that the $3^{rd}$ note C4 is on the other side.

If in a main-auxiliary bilateral electrode mode, for the melody section A3, G3 and C4, because the fundamental frequencies are distributed on the main side, the three notes work on the main side cochlea electrodes in sequence, wherein the specific working condition is shown in table 4.3.

TABLE 4.1

$1^{st}$ (A3) and $2^{nd}$ (G3) notes sequentially work on electrodes in equalization binaural mode (on one side)

| No. | Note | Center frequency | Pass band range |
|---|---|---|---|
| 36 | A1 | 55 | 52.6-57.4 |
| 35 | E2 | 82.407 | 80.0-84.8 |
| 34 | C3 | 130.8 | 127.1-134.5 |
| 33 | G3 | 196.00 | 190.3-201.7 |
| 32 | A3 | 220.00 | 213.6-226.4 |
| 31 | B3 | 246.94 | 239.8-254.1 |
| 30 | C#/Db4 | 277.18 | 269.1-285.2 |
| 29 | D#/Eb4 | 311.13 | 302.3-320.2 |
| 28 | F4 | 349.23 | 339.1-359.4 |
| 27 | G4 | 392.00 | 380.6-403.4 |

TABLE 4.1-continued

1st (A3) and 2nd (G3) notes sequentially work on electrodes in equalization binaural mode (on one side)

| No. | Note | Center frequency | Pass band range |
|---|---|---|---|
| 26 | A4 | 440.00 | 427.2-452.8 |
| 25 | B4 | 493.88 | 479.5-508.2 |
| 24 | C#/Db5 | 544.37 | 538.3-570.5 |
| 23 | D#/Eb5 | 622.25 | 604.1-640.5 |
| 22 | F5 | 698.46 | 678.1-718.9 |
| 21 | G5 | 783.99 | 761.1-806.9 |
| 20 | A5 | 880.00 | 854.3-905.7 |
| 19 | B5 | 987.77 | 958.9-1016.7 |
| 18 | C#/Db6 | 1108.70 | 1076.3-1141.1 |
| 17 | D#/Eb6 | 1244.50 | 1208.3-1280.7 |
| 16 | F6 | 1396.90 | 1356.3-1437.5 |
| 15 | G6 | 1568.00 | 1522.5-1613.5 |
| 14 | A6 | 1760.00 | 1708.9-1811.1 |
| 13 | B6 | 1975.50 | 1918.3-2032.7 |
| 12 | C#/Db7 | 2217.50 | 2153.3-2281.7 |
| 11 | D#/Eb7 | 2489.00 | 2416.9-2561.1 |
| 10 | F7 | 2793.80 | 2712.9-2874.7 |
| 9 | G7 | 3136.00 | 3045.3-3226.7 |
| 8 | A7 | 3520.00 | 3418.1-3621.9 |
| 7 | B7 | 3951.10 | 3836.7-4065.5 |
| 6 | C#/Db8 | 4434.00 | 4306.5-4563.3 |
| 5 | D#/Eb8 | 4978.00 | 4833.9-5122.1 |
| 4 | F8 | 5587.70 | 5425.9-5749.5 |
| 3 | G8 | 6271.90 | 6090.1-6453.7 |
| 2 | A8 | 7040.00 | 6835.7-7244.3 |
| 1 | B8 | 7902.10 | 7672.8-8131.4 |

TABLE 4.2

3rd (C4) note works on electrodes in equalization binaural mode (on the other side)

| No. | Note | Center frequency | Pass band range |
|---|---|---|---|
| 36 | A1 | 55 | 52.6-57.4 |
| 35 | E2 | 82.407 | 80.0-84.8 |
| 34 | C3 | 130.8 | 127.1-134.5 |
| 32 | G#/Ab3 | 207.65 | 201.7-213.6 |
| 31 | A#/Bb3 | 233.08 | 226.4-239.8 |
| 30 | C4 | 261.63 | 254.1-261.1 |
| 29 | D4 | 293.66 | 285.2-302.1 |
| 28 | E4 | 329.6 | 320.2-339.1 |
| 27 | F#/Eb4 | 369.99 | 359.4-380.6 |
| 26 | G#/Ab4 | 415.3 | 403.4-427.2 |
| 25 | A#/Bb4 | 466.16 | 452.8-479.5 |
| 24 | C5 | 523.25 | 508.2-538.3 |
| 23 | *D5* | *587.33* | *570.5-604.1* |
| 22 | E5 | 659.2 | 640.5-678.1 |
| 21 | F#/Eb5 | 739.99 | 718.9-761.1 |
| 20 | G#/Ab5 | 830.61 | 806.9-854.3 |
| 19 | A#/Bb5 | 932.33 | 905.7-958.9 |
| 18 | C6 | 1046.5 | 1016.7-1076.3 |
| 17 | *D6* | *1174.7* | *1141.1-1208.3* |
| 16 | E6 | 1318.5 | 1280.7-1356.3 |
| 15 | F#/Eb6 | 1480.00 | 1437.5-1522.5 |
| 14 | G#/Ab6 | 1661.2 | 1613.5-1708.9 |
| 13 | A#/Bb6 | 1864.7 | 1811.1-1918.3 |
| 12 | C7 | 2093 | 2032.7-3045.3 |
| 11 | D7 | 2349.3 | 2281.7-2416.9 |
| 10 | E7 | 2637 | 2561.1-2712.9 |
| 9 | F#/Eb7 | 2960 | 2874.7-3045.3 |
| 8 | G#/Ab7 | 3322.4 | 3226.7-3418.1 |
| 7 | A#/Bb7 | 3729.3 | 3621.9-3836.7 |
| 6 | C8 | 4186 | 4065.5-4306.5 |
| 5 | D8 | 4698.6 | 4563.3-4833.9 |
| 4 | E8 | 5274 | 5122.1-5425.9 |
| 3 | F#/Eb8 | 5919.9 | 5749.5-6090.3 |
| 2 | G#/Ab8 | 6644.9 | 6454-6835.8 |
| 1 | A#/Bb8 | 7458.6 | 7245.1-7672.1 |

TABLE 4.3

1st (A3), 2nd (G3) and 3rd (C4) note works on electrodes in main-auxiliary bilateral mode (sequentially on main side)

| No. | Note | Center frequency | Pass band range |
|---|---|---|---|
| 41 | A1 | 55 | 52.6-57.4 |
| 40 | E2 | 82.407 | 80.0-84.8 |
| 39 | C3 | 130.8 | 127.1-134.5 |
| 38 | G3 | 196.00 | 190.3-201.7 |
| 37 | A3 | 220.00 | 213.6-226.4 |
| 36 | B3 | 246.94 | 239.8-254.1 |
| 35 | C4 | 261.63 | 254.1-261.1 |
| 34 | D4 | 293.66 | 285.2-302.1 |
| 33 | E4 | 329.6 | 320.2-339.1 |
| 32 | F4 | 349.23 | 339.1-359.4 |
| 31 | G4 | 392.00 | 380.6-403.4 |
| 30 | A4 | 440.00 | 427.2-452.8 |
| 29 | B4 | 493.88 | 479.5-508.2 |
| 28 | C5 | 523.25 | 508.2-538.3 |
| 27 | D5 | 587.33 | 570.5-604.1 |
| 26 | E5 | 659.2 | 640.5-678.1 |
| 25 | F5 | 698.46 | 678.1-718.9 |
| 24 | G5 | 783.99 | 761.1-806.9 |
| 23 | A5 | 880.00 | 854.3-905.7 |
| 22 | B5 | 987.77 | 958.9-1016.7 |
| 21 | C6 | 1046.5 | 1016.7-1076.3 |
| 20 | D6 | 1174.7 | 1141.1-1208.3 |
| 19 | E6 | 1318.5 | 1280.7-1356.3 |
| 18 | F6 | 1396.90 | 1356.3-1437.5 |
| 17 | G6 | 1568.00 | 1522.5-1613.5 |
| 16 | A6 | 1760.00 | 1708.9-1811.1 |
| 15 | B6 | 1975.50 | 1918.3-2032.7 |
| 14 | C7 | 2093 | 2032.7-3045.3 |
| 13 | D7 | 2349.3 | 2281.7-2416.9 |
| 12 | E7 | 2637 | 2561.1-2712.9 |
| 11 | F7 | 2793.80 | 2712.9-2874.7 |
| 10 | G7 | 3136.00 | 3045.3-3226.7 |
| 9 | A7 | 3520.00 | 3418.1-3621.9 |
| 8 | B7 | 3951.10 | 3836.7-4065.5 |
| 7 | C8 | 4186 | 4065.5-4306.5 |
| 6 | D8 | 4698.6 | 4563.3-4833.9 |
| 5 | E8 | 5274 | 5122.1-5425.9 |
| 4 | F8 | 5587.70 | 5425.9-5749.5 |
| 3 | G8 | 6271.90 | 6090.1-6453.7 |
| 2 | A8 | 7040.00 | 6835.7-7244.3 |
| 1 | B8 | 7902.10 | 7672.8-8131.4 |

In addition, with the development of technology, when the arrangement of cochlea electrodes is not limited by the realizing process, it is the most ideal design that all the frequency points in tables 2.1 and 2.2 are arranged in the unilateral cochlea, and when all the electrodes are arranged in a unilateral ear, said cochlear implant device and corresponding optimization system are still applicable.

The text of above provide electrode distribution on one side in bilateral equalization or electrode distribution on main side in main-auxiliary scheme according to the characteristic frequency correspondence of music notes. And according to user requirements, the invention can provide flexible single or bilateral electrode combinations, for example: an equalization unilateral electrode implant one side electrode array, or an equalization bilateral electrode implant both sides electrode array, or main electrode of the main-auxiliary unilateral electrode implant one side electrode array, or two of the same main electrodes implant and then insert into both sides electrode array, or a main electrode and auxiliary electrode matched up are implanted in both sides electrode array. After implantation into the electrode array, the user need to determine whether the electrode number corresponds to the characteristic frequency. And it is used in combination with various coding schemes of external sound processor.

Although the specific embodiments of the present invention are described above in combination with the accompanying drawings, the protection scope of the present invention is not limited thereto. It should be appreciated by those skilled in the art that various modifications or variations made by those skilled in the art without any creative effort based on the technical solution of the present invention shall fall into the protection scope of the present invention.

The invention claimed is:

1. A cochlear implant sound processing system having a cochlea electrode arrangement for enhancing musical melody perception, comprising:
a plurality of electrodes for transmitting frequency band signals, the plurality of electrodes being divided into a first group of electrodes and a second group of electrodes,
wherein the first group of electrodes is implanted into a first cochleae of bilateral cochleae on a first side, and the second group of electrodes is implanted into a second cochleae of the bilateral cochleae on a second side;
wherein for a cochlear basilar membrane on each of the first side and the second side, according to a characteristic frequency correspondence of musical notes, a phonosensitive full spectrum band corresponding to a cochlea apex to a cochlea base is divided into frequency areas corresponding to specific notes,
wherein the electrodes are configured to be arranged in one of two electrode distribution configurations including an equalization configuration or a main-auxiliary configuration, the equalization configuration and the main-auxiliary configuration being adopted for bilateral ears by using characteristics of dual ears and dual tracks,
wherein each of the first group and the second group of electrodes includes more than 22 electrodes, which are placed in each frequency area, each electrode being placed in a characteristic frequency band where the musical notes are located, and each electrode corresponding to a fundamental wave frequency point of a different note,
wherein in the equalization configuration, the number of electrodes of the first group is equal to the number of electrodes of the second group, and the electrodes of each of the first group and the second group are arranged into electrode arrays in an equal-pitch interval alternating manner at set frequency bands,
wherein representative frequency points are selected and respectively arranged at corresponding positions nearby the bilateral cochlea apexes,
wherein each of the first group and the second group of electrodes includes 33 electrodes, which are implanted into frequency areas, other than low frequency areas, in each of the first cochlea on the first side and the second cochlea on the second side, respectively,
wherein on the first side, the 33 electrodes are implanted into the first cochlea such that the $1^{st}$ electrode corresponds to the fundamental wave frequency of a B8 note, the $33^{rd}$ electrode corresponds to the fundamental wave frequency of a G3 note, and the electrodes between the $1^{st}$ electrode and the $33^{rd}$ electrode are arranged according to a whole-tone frequency interval,
wherein on the second side, the 33 electrodes are implanted into the second cochlea such that the $1^{st}$ electrode corresponds to the fundamental wave frequency of a C9 note, the $33^{rd}$ electrode corresponds to the fundamental wave frequency of a G#/Ab3 note, and the electrodes between the $1^{st}$ electrode and the $33^{rd}$ electrode are arranged according to a whole-tone note frequency interval,
wherein each of the first group and the second group of electrodes includes three electrodes, which are in the low frequency areas of each the first cochlea and the second cochlea, respectively, such that the $36^{th}$ electrode corresponds to the fundamental wave frequency of an A1 note, the $35^{th}$ electrode corresponds to the fundamental wave frequency of an E2 note, and the $34^{th}$ electrode corresponds to the fundamental wave frequency of a C3 note,
wherein in the main-auxiliary configuration, the number of electrodes of the first group is different from the number of electrodes in the second group, and are arranged into electrode arrays in a specified frequency interval alternating manner at set frequency bands,
wherein at the low frequency areas, corresponding representative frequency points are selected for arranging corresponding electrodes, the electrodes being respectively implanted into the bilateral cochleae, and each of the first group and the second group of electrodes includes three electrodes, which are implanted in the low frequency areas of each the first cochlea and the second cochlea, respectively,
wherein when the number of electrodes of the first group is different from the number numbers of electrodes in the second group, the first group being a main electrode group of 38 electrodes of the plurality of electrodes and the second group being an auxiliary electrode group of 27 electrodes of the plurality of electrodes, the main electrode group is distributed in correspondence to a main frequency sensing area of the first cochlea on the first side, and the auxiliary electrode group is distributed in correspondence to a main frequency sensing area of the second cochlea on the second side,
wherein in the first cochlea, the main electrode group is distributed in such that:
the $1^{st}$ electrode corresponds to the fundamental wave frequency of the B8 note;
the $38^{th}$ electrode corresponds to the fundamental wave frequency of the G3 note; and
the electrodes between the $1^{st}$ electrode and the $38^{th}$ electrode are arranged according to a note frequency correspondence in a set manner,
wherein in the second cochlea, the auxiliary electrode group is distributed such that:
the $1^{st}$ electrode corresponds to the fundamental wave frequency of an A#/Bb8 note;
the $27^{th}$ electrode corresponds to the fundamental wave frequency of the G#/Ab3 note; and
the electrodes between the $1^{st}$ electrode and the $27^{th}$ electrode are arranged according to the note frequency correspondence in a set manner,
wherein in the low frequency areas, each of the first group and the second group of electrodes includes three electrodes, which are respectively distributed, as follows:
in the main electrode group, the $41^{st}$ electrode corresponds to the fundamental wave frequency of the A1 note, the $40^{th}$ electrode corresponds to the fundamental wave frequency of the E2 note, and the $39^{th}$ electrode corresponds to the fundamental wave frequency of the C3 note; and
in the auxiliary electrode group, the $30^{th}$ electrode corresponds to the fundamental wave frequency of the A1 note, the $29^{th}$ electrode corresponds to the fundamental wave frequency of the E2 note, and the 28$^{th}$ electrode corresponds to the fundamental wave frequency of the C3 note.

2. A cochlear implant sound processing method for enhancing musical melody perception, comprising:
dividing a plurality of electrodes into a first group and a second group, each of the first group and the second group including more than 22 electrodes, and implanting the first group of electrodes into a first cochleae of bilateral cochleae, and implanting the second group of electrodes into a second cochleae of the bilateral cochleae;
arranging each electrode arranged in a corresponding characteristic frequency band where musical notes are located, each electrode corresponding to a fundamental wave frequency point of a different note, the electrodes being mainly concentrated in main frequency sensing areas of 100 Hz-8000 Hz, and corresponding representative frequency points being selected for arranging the electrodes in low frequency areas,
wherein the electrodes are configured to be arranged in one of an equalization configuration or a main-auxiliary configuration,
wherein in the equalization configuration, the number of electrodes of the first group is equal to the number of electrodes of the second group, and the method further comprises arranging the electrodes in a left-right staggered and equal interval manner in a unilateral cochlea according to fundamental wave characteristic frequencies of notes in the main frequency sensing areas,
wherein in the main-auxiliary configuration, the number of electrodes of the first group is not equal to the number of electrodes in the second group the electrodes being arranged in the unilateral cochlea according to fundamental wave characteristic frequencies of notes in a set manner, and
wherein each of the first group and the second group of electrodes includes 33 electrodes, which are implanted into frequency areas, other than low frequency areas, in each of the first cochlea on a first side and the second cochlea on a second side, respectively;
implanting, on the first side, the 33 electrodes the first cochlea such that the 1st electrode corresponds to the fundamental wave frequency of a B8 note, the 33rd electrode corresponds to the fundamental wave frequency of a G3 note, and the electrodes between the 1st electrode and the 33rd electrode are arranged according to a whole-tone frequency interval; and
implanting, on the second side, the 33 electrodes into the second cochlea such that the 1$^{st}$ electrode corresponds to the fundamental wave frequency of a C9 note, the 33rd electrode corresponds to the fundamental wave frequency of a G#/Ab3 note, and the electrodes between the 1st electrode and the 33rd electrode are arranged according to a whole-tone note frequency interval,
wherein each of the first group and the second group of electrodes includes three electrodes, which are in the low frequency areas of each the first cochlea and the second cochlea, respectively, such that the 36th electrode corresponds to the fundamental wave frequency of an A1 note, the 35th electrode corresponds to the fundamental wave frequency of an E2 note, and the 34th electrode corresponds to the fundamental wave frequency of a C3 note,
wherein in the main-auxiliary configuration, the number of electrodes of the first group is different from the number of electrodes in the second group, and are arranged into electrode arrays in a specified frequency interval alternating manner at set frequency bands,
wherein at the low frequency areas, corresponding representative frequency points are selected for arranging corresponding electrodes, the electrodes being respectively implanted into the bilateral cochleae, and each of the first group and the second group of electrodes includes three electrodes, which are implanted in the low frequency areas of each the first cochlea and the second cochlea, respectively,
wherein when the number of electrodes of the first group is different from the number numbers of electrodes in the second group, the first group being a main electrode group of 38 electrodes of the plurality of electrodes and the second group being an auxiliary electrode group of 27 electrodes of the plurality of electrodes, the main electrode group is distributed in correspondence to a main frequency sensing area of the first cochlea on the first side, and the auxiliary electrode group is distributed in correspondence to a main frequency sensing area of the second cochlea on the second side,
wherein in the first cochlea, the main electrode group is distributed in such that:
the 1st electrode corresponds to the fundamental wave frequency of the B8 note;
the 38th electrode corresponds to the fundamental wave frequency of the G3 note; and
the electrodes between the 1st electrode and the 38th electrode are arranged according to a note frequency correspondence in a set manner,
wherein in the second cochlea, the auxiliary electrode group is distributed such that:
the 1st electrode corresponds to the fundamental wave frequency of an A#/Bb8 note;
the 27th electrode corresponds to the fundamental wave frequency of the G#/Ab3 note; and
the electrodes between the 1st electrode and the 27th electrode are arranged according to the note frequency correspondence in a set manner,
wherein in the low frequency areas, each of the first group and the second group of electrodes includes three electrodes, which are respectively distributed, as follows:
in the main electrode group, the 41st electrode corresponds to the fundamental wave frequency of the A1 note, the 40th electrode corresponds to the fundamental wave frequency of the E2 note, and the 39th electrode corresponds to the fundamental wave frequency of the C3 note; and
in the auxiliary electrode group, the 30th electrode corresponds to the fundamental wave frequency of the A1 note, the 29th electrode corresponds to the fundamental wave frequency of the E2 note, and the 28th electrode corresponds to the fundamental wave frequency of the C3 note.

3. The cochlear implant sound processing system according to claim 1,
wherein each of the plurality of electrodes comprises:
a plurality of annular electrode contacts connected to electrode circuits via metal wires with insulating layers; and
a flexible envelope that wraps the electrode circuits, and
wherein the electrodes are arranged into arrays.

4. The cochlear implant sound processing system according to claim 3, further comprising:

an implant part and an external part,
wherein the implant part and the external part are configured to adopt a wireless communication connection mode or a wired connection mode,
wherein the implant part comprises an electrode array device, which includes the electrodes arranged into arrays,
wherein the external part comprises a sound processor and a sound acquisition device connected to the sound processor, and
wherein sound signals are acquired by the sound acquisition device, notes and pitch intervals of a main melody of music signals are analyzed and coded by the sound processor, corresponding MIDI music codes are generated by the sound processor according to a type of a musical instrument and converted into bilateral cochlea electrode stimulating coded signals via a corresponding processing algorithm, and the stimulating coded signals are transmitted to stimulated parts via wireless communication or dedicated wired interface drive.

5. The cochlear implant sound processing system according to claim 4,
wherein for the wireless communication connection mode, the electrode array device and a receiving device serve as the implant part of a cochlear implant, and
wherein a transmitter, the sound processor and the sound acquisition device serve as the external part of the cochlear implant.

6. The cochlear implant sound processing system according to claim 4,
wherein for the wired connection mode, the electrode array device serves as the implant part of a cochlear implant,
wherein a wired interface device, a signal drive device, the sound processor and the sound acquisition device serve as the external part, and
wherein signals acquired by the sound acquisition device are transmitted to the sound processor, the sound processor decomposes and quantifies the acquired signals to generate corresponding signals and transmits the signals to the signal drive device, the signal drive device transits each path of signals generated by drive to the wired interface device, and each path of signals is connected with each path of signals of implanted electrodes at the wired interface device to generate corresponding stimulating signals.

7. The cochlear implant sound processing system for enhancing musical melody perception according to claim 4,
wherein the wireless communication mode of the implant part and the external part is one of: a Bluetooth® communication mode, an infrared communication mode, or a radio frequency (RF) communication mode, and
wherein the wired connection mode includes use of a connection structure wrapped by a flexible material, and the connection structure being an optical connection structure, a thermal connection structure, or a mechanical connection structure.

8. The cochlear implant sound processing method for enhancing musical melody perception according to claim 2, further comprising:
transmitting signals acquired by a sound acquisition device to a sound processor;
analyzing and encoding, by the sound processor, notes and pitch intervals of a main melody of the music signals;
generating, by the sound processor, corresponding MIDI music codes according to a type of a musical instrument, and the codes being processed by the sound processor via a processing algorithm corresponding to a mode;
determining, by the sound processor, the location of an effective working electrode of each note according to the electrode working mode;
determining, by the sound processor, an array on each side and each electrode coding sequence; and
converting, by the sound processor, the music codes into bilateral cochlea electrode stimulating coded signals via the processing algorithm corresponding to the mode, and the stimulating coded signals being transmitted to stimulated parts via wireless communication or a dedicated wired interface drive.

* * * * *